United States Patent
Stepp et al.

(10) Patent No.: US 10,441,930 B2
(45) Date of Patent: Oct. 15, 2019

(54) METHOD FOR PRODUCING PULVERULENT SOLIDS FROM ALKALI SALTS OF SILANOLS

(71) Applicant: Wacker Chemie AG, Munich (DE)

(72) Inventors: Michael Stepp, Ueberackern (AT); Daniel Schildbach, Helmstadt (DE)

(73) Assignee: WACKER CHEMIE AG, Munich (DE)

( * ) Notice: Subject to any disclaimer, the term of this patent is extended or adjusted under 35 U.S.C. 154(b) by 40 days.

(21) Appl. No.: 15/557,112

(22) PCT Filed: Feb. 19, 2016

(86) PCT No.: PCT/EP2016/053603
§ 371 (c)(1),
(2) Date: Sep. 10, 2017

(87) PCT Pub. No.: WO2016/142155
PCT Pub. Date: Sep. 15, 2016

(65) Prior Publication Data
US 2018/0043324 A1 Feb. 15, 2018

(30) Foreign Application Priority Data
Mar. 10, 2015 (DE) .......................... 10 2015 204 263

(51) Int. Cl.
| | | |
|---|---|---|
| *B01J 2/04* | (2006.01) | |
| *C04B 24/42* | (2006.01) | |
| *C04B 28/02* | (2006.01) | |
| *C04B 28/14* | (2006.01) | |
| *C09D 7/63* | (2018.01) | |
| *C09D 5/03* | (2006.01) | |
| *C07F 7/18* | (2006.01) | |
| *C04B 103/00* | (2006.01) | |
| *C04B 103/65* | (2006.01) | |
| *C04B 111/27* | (2006.01) | |

(52) U.S. Cl.
CPC ................. *B01J 2/04* (2013.01); *C04B 24/42* (2013.01); *C04B 28/02* (2013.01); *C04B 28/14* (2013.01); *C07F 7/1804* (2013.01); *C09D 5/03* (2013.01); *C09D 7/63* (2018.01); *C04B 2103/0057* (2013.01); *C04B 2103/65* (2013.01); *C04B 2111/27* (2013.01)

(58) Field of Classification Search
CPC ... B01J 2/04; C09D 7/63; C04B 24/42; C04B 28/02; C04B 28/14
See application file for complete search history.

(56) References Cited

U.S. PATENT DOCUMENTS

| | | |
|---|---|---|
| 2,438,055 A | 3/1948 | Hyde et al. |
| 2,567,110 A | 9/1951 | Hyde et al. |
| 2,803,561 A | 8/1957 | Kather |
| 8,748,645 B2 | 6/2014 | Schildbach et al. |
| 8,961,672 B2 | 2/2015 | Stepp et al. |
| 9,200,013 B2 | 12/2015 | Stepp et al. |
| 2014/0228589 A1 | 8/2014 | Stepp et al. |
| 2015/0284413 A1 | 10/2015 | Stepp et al. |
| 2017/0137445 A1* | 5/2017 | Stepp .................... C07F 7/0836 |

FOREIGN PATENT DOCUMENTS

| | | | |
|---|---|---|---|
| DE | 1176137 B | 8/1964 | |
| DE | 4336600 C1 | 10/1994 | |
| DE | 102011076303 A1 | 11/2012 | |
| DE | 102011076344 A1 | 11/2012 | |
| WO | 2012022544 A1 | 2/2012 | |
| WO | WO-2012159874 A1 * | 11/2012 | ........... C04B 41/009 |
| WO | 2013041385 A1 | 3/2013 | |
| WO | 2013075969 A1 | 5/2013 | |
| WO | 2013174689 A1 | 11/2013 | |
| WO | 2015176977 A1 | 11/2015 | |

* cited by examiner

*Primary Examiner* — Melvin C. Mayes
*Assistant Examiner* — Michael Forrest
(74) *Attorney, Agent, or Firm* — Brooks Kushman P.C.

(57) ABSTRACT

Pulverulent alkali metal alkyl siliconates having lesser hydroscopicity and improved hydrophobicity in construction materials are produced by spray drying an aqueous solution of an alkali metal alkylsiliconate having a defined range of alkali metal content, a low alcohol content, and a low chlorine content.

4 Claims, No Drawings

METHOD FOR PRODUCING PULVERULENT SOLIDS FROM ALKALI SALTS OF SILANOLS

CROSS REFERENCE TO RELATED APPLICATIONS

This application is the U.S. National Phase of PCT Appln. No. PCT/EP2016/053603 filed Feb. 19, 2016, which claims priority to German Application No. 10 2015 204 263.4 filed Mar. 10, 2015, the disclosures of which are incorporated in their entirety by reference herein.

BACKGROUND OF THE INVENTION

1. Field of the Invention

The invention relates to a process for producing pulverulent solids comprising alkali metal organosiliconates for hydrophobicizing building materials.

2. Description of the Related Art

The alkali metal organosiliconates are also referred to as alkali metal salts of organosilicic acids. Alkali metal organosiliconates such as potassium, methyl siliconate have been used for decades for hydrophobization, in particular for mineral building materials. Owing to their good solubility in water, they can be applied as an aqueous solution to solids where, after evaporation of the water, they form firmly adhering, lastingly water-repellent surfaces as a result of pH-changing effects, e.g. reaction with carbon dioxide, Since they contain virtually no hydrolytically eliminatable organic radicals, curing advantageously occurs without liberation of undesirable volatile, organic by-products.

The preparation of alkali metal organosiliconates, in particular potassium and sodium methyl siliconates, has been described many times. In most cases, the focus is on the preparation of ready-to-use and storage-stable, aqueous solutions.

In U.S. Pat. No. 2,803,561, alkyltrichlorosilane is hydrolyzed to the corresponding alkylsilicic acid and the latter is subsequently reacted with alkali metal hydroxide; to give an aqueous solution of alkali metal silioonate, which is stabilized by addition of alcohol or ketone.

The complicated isolation and purification of the solid can be circumvented in the continuous process described in DS 4336600 starting out from, organotrichlorosilanes via an intermediate organotrialkoxysilane which is finally reacted with alkali metal hydroxide. An advantage is that the hydrogen chloride and alcohol by-products which are formed are recovered and the siliconate solution formed is virtually free of chlorine.

Ready-to-use building material mixtures such as cement or gypsum plasters and renders, and knifing fillers or tile adhesives, are delivered to building sites mainly as powder in bags or silos and mixed with the make-up water on-site. This requires a solid hydrophobicizing agent which can be added to the ready-to-use dry mixture and only displays its hydrophobizing action in a short time after addition of water during application on site, e.g. on the building site. This is referred to as "dry mix" use. Organosiliconates in solid form have been found to be very efficient hydrophobizing additives for this purpose. Nevertheless, only few industrially practicable processes for producing these have hitherto been published.

WO 2013/174689 describes the preparation of solid alkali metal organosiliconates from their aqueous solutions by means of an inert liquid (azeotropic entrainer). A disadvantage is the large amount of flammable auxiliary which is covaporized and circulated, which is very troublesome in terms of plant construction and safety, and also results in emissions. In addition, this liquid has to be removed again in a time- and energy-consuming manner in order to isolate the solid.

In the patent literature, direct drying processes for aqueous and/or alcoholic solutions are described in processes which are either based on a complicated crystallization (U.S. 2,438,055) or an input of heat with a short residence time (DE 1176137: 350-400° C., 2-3 minutes) (U.S. Pat. No. 2,567,110: 170° C. "to constant weight"). Disadvantages of these processes are the complicated industrial implementation and the risk of thermal decomposition with a very high energy potential. In WO 2013/041385, this problem can be overcome by means of a two-stage process for the direct drying of aqueous/alcoholic siliconate solutions, but viscous intermediate states which place great engineering demands on the dryer are passed through during the drying process. Drying in a powder bed composed of previously dried siliconate has also been described (WO 2013/075969), but this is likewise technically demanding and time-consuming and runs counter to the limited thermal stability of the alkali metal siliconates.

SUMMARY OF THE INVENTION

The invention provides a process for producing pulverulent solids (S) comprising alkali metal organosiliconates, wherein water is removed from, aqueous solutions of alkali metal organosiliconates having a molar ratio of alkali metal to silicon of from 0.1 to 3, a content of alcohol of less than 0.1% by weight and a content of halide anions of not more than 1% by weight, by spray drying.

DETAILED DESCRIPTION OF THE PREFERRED EMBODIMENTS

As a result of the removal of water from the aqueous solutions, the solid alkali metal organosiliconates are obtained directly as very free-flowing powders (S). It was surprising that, despite the viscous intermediate states described in the prior art during drying of siliconate solutions, spray drying led to the objective. It was also found that the solid alkali metal siliconates which have been dried according to the invention display a significantly less pronounced hygroscopic behavior compared to the alkali metal siliconate powders produced according to the prior art, which can easily be determined via the percentage increase in weight during storage under defined conditions (humidity, temperature).

Simple and complete recycling of the dissociation product formed in the preparation of the alkali metal organosiliconates in the hydrolysis step, preferably alcohol or hydrogen halide, is possible in the process. As indicated in, for example, WO 12022544, long drying times at high temperatures should be avoided because of the thermal instability of the aqueous siliconate solutions. Owing to the very short thermal stressing, the gentle spray drying process is particularly well-suited for this purpose.

The molar ratio of alkali metal to silicon in the aqueous solutions of the alkali metal organosiliconates is preferably at least 0.3, in particular at least 0.5, and not more than 2, in particular not more than 1.2. The content of alcohols in the aqueous solutions of the alkali metal organosiliconates is preferably less than 0.05% by weight, more preferably less than 0.02% by weight, and in particular less than 0.01% by weight. The content of halide anions in the aqueous solutions of the alkali metal organosiliconates is preferably not more than 0.3% by weight, more preferably not more than 0.1% by weight, and in particular not more than 0.01% by weight.

The aqueous solutions of the alkali metal organosiliconates are in many cases commercially available and can, for example, be prepared by means of known methods by reaction of one or more organosilanes of the general formula 1

(1)

or hydrolysis/condensation products thereof, or by reaction of the organosilanes of the general formula 1 together with hydrolysis/condensation products thereof,
with water and a basic alkali metal salt and removal of the dissociation products HY liberated,
where
$R^1$, $R^2$ are each a monovalent Si—C-bonded hydrocarbon radical which has from 1 to 8 carbon atoms and is unsubstituted or substituted by halogen atoms, amino groups, thiol groups, silyl groups substituted by $C_{1-6}$-alkyl or $C_{1-6}$-alkoxy groups, in which one or more, nonadjacent —$CH_2$— units can be replaced by —O—, —S— or —$NR^3$— groups and in which one or more, nonadjacent =CH— units can be replaced by =N= groups,
Y is hydrogen, F, Cl, Br or $OR^4$
$R^4$ is a methyl, ethyl, 1-propyl or 2-propyl group,
a is 1, 2 or 3 and
b, c, d are each 0, 1, 2 or 3,
with the proviso that b+c≥1 and a+b+d=4,
where the amount of basic alkali metal salt is such that there is at least 0.1 mol, more preferably at least 0.3 mol, and in particular at least 0.5 mol, and not more than 3 mol, more preferably not more than 2 mol, and in particular not more than 1.2 mol, of alkali metal cations per 1 mol of silicon.

It is also possible to use mixtures of these organosilanes of the general formula 1 or mixed oligomers of compounds of the general formula 1, or mixtures of these mixed oligomeric siloxanes with monomelic organosilanes of the general formula 1. Any silanol groups formed by hydrolysis which may be present in the compounds of the general formula 1 or oligomers thereof do not interfere.

$R^1$, $R^2$ can be linear, branched, cyclic, aromatic, saturated or unsaturated. Examples of amino groups in $R^1$, $R^2$ are —$NR^5R^6$ radicals, where $R^5$ and $R^6$ are each hydrogen, a $C_1$-$C_8$-alkyl radical, cycloalkyl, aryl, arylalkyl, alkylaryl which may be substituted by —$OR^7$, where $R^7$ can be $C_1$-$C_8$-alkyl, aryl, arylalkyl, alkylaryl. If $R^5$, $R^6$ are alkyl radicals, nonadjacent $CH_2$— units therein can be replaced by —O—, —S— or —$NR^3$— groups. $R^5$ and $R^6$ can also represent a ring. $R^5$ is preferably hydrogen or an alkyl radical having from 1 to 6 carbon atoms.

$R^1$, $R^2$ in the general formula 1 are each preferably a monovalent hydrocarbon radical which has from 1 to 18 carbon atoms and may be unsubstituted or substituted by halogen atoms, amino, alkoxy or silyl groups. Particular preference is given to unsubstituted alkyl radicals, cycloalkyl radicals, alkylaryl radicals, arylalkyl radicals and phenyl radicals. The hydrocarbon radicals $R^1$, $R^2$ preferably nave from 1 to 6 carbon atoms; $R^1$, $R^2$ are preferably each an alkyl radical having from 1 to 6 carbon atoms. Particular preference is given to the methyl, ethyl, propyl, 3,3,3-trifluoropropyl, 3-aminopropyl, 3-(2-aminoethyl)aminopropyl, vinyl, n-hexyl and phenyl radicals, most preferably the methyl radical.

Further examples of radicals $R^1$, $R^2$ are:
n-propyl, 2-propyl, 3-chloropropyl, 2-(trimethylsilyl)ethyl, 2-(trimethoxysilyl)ethyl, 2-(triethoxysilyl)ethyl, 2-(dimethoxy-methylsilyl)ethyl, 2-(diethoxymethylsilyl)ethyl, n-butyl, 2-butyl, 2-methylpropyl, t-butyl, n-pentyl, cyclopentyl, n-hexyl, cyclohexyl, n-heptyl, n-octyl, 2-ethylhexyl, n-nonyl, n-decyl, n-undecyl, 10-undecenyl, n-dodecyl, isotridecyl, n-tetradecyl, n-hexadecyl, vinyl, allyl, benzyl, p-chlorophenyl, o-(phenyl)-phenyl, m-(phenyl)phenyl, p-(phenyl)phenyl, 1-naphthyl, 2-naphthyl, 2-phenylethyl, 1-phenylethyl, 3-phenylpropyl, N-morpholinomethyl, N-pyrrolidinomethyl, 3-(N-cyclohexyl)-aminopropyl, 1-N-imidazolidinopropyl radicals.

Further examples of $R^1$, $R^2$ are —$(CH_2O)_n$—$R^8$, —$(CH_2CH_2O)_m$—$R^9$ and —$(CH_2CH_2NH)_o$H, —$(CH_2CH(CH_3)O)_p$—$R^{10}$ radicals, where n, m, o and p are from 1 to 10, in particular 1, 2, 3, and $R^8$, $R^9$ and $R^{10}$ have the meanings of $R^5$, $R^6$.

$R^3$ is preferably hydrogen, a monovalent hydrocarbon radical which has from 1 to 8 carbon atoms and is unsubstituted or substituted by halogen atoms or $NH_2$ groups. Examples of $R^3$ have been indicated above for $R^1$.

d is preferably 0. d is preferably 1, 2 or 3 in not more than 20 mol %, in particular not more than 5 mol %, of the compounds of the general formula 1.

Examples of compounds of the general formula 1 in which a=1 are:
$MeSi(OMe)_3$, $MeSi(OEt)_3$, $MeSi(OMe)_2(OEt)$, $MeSi(OMe)(OEt)_2$, $MeSi(OCH_2CH_2OCH_3)_3$, $H_3C$—$CH_2$—$CH_2$—$Si(OMe)_3$, $(H_3C)_2CH$—$Si(OMe)_3$, $CH_3CH_2CH_2CH_2$—$Si(OMe)_3$, $(H_3C)_2CHCH_2$—$Si(OMe)_3$, $tBu$-$Si(OMe)_3$, $PhSi(OMe)_3$, $PhSi(OEt)_3$, $F_3C$—$CH_2$—$CH_2$—$Si(OMe)_3$, $H_2C$=$CH$—$Si(OMe)_3$, $H_2C$=$CH$—$Si(OEt)_3$, $H_2C$=$CH$—$CH_2$—$Si(OMe)_3$, $Cl$—$CH_2CH_2CH_2$—$Si(OMe)_3$, n-Hex-$Si(OMe)_3$, cy-Hex-$Si(OEt)_3$, cy-Hex-$CH_2$—$CH_2$—$Si(OMe)_3$, $H_2C$=$CH$—$(CH_2)_9$—$Si(OMe)_3$, $CH_3CH_2CH_2CH_2CH(CH_2CH_3)$—$CH_2$—$Si(OMe)_3$, hexadecyl-$Si(OMe)_3$, $Cl$—$CH_2$—$Si(OMe)_3$, $H_2N$—$(CH_2)_3$—$Si(OEt)_3$, cyHex-NH—$(CH_2)_3$—$Si(OMe)_3$, $H_2N$—$(CH_2)_2$—NH—$(CH_2)_3$—$Si(OMe)_3$, $O(CH_2CH_2)_2N$—$CH_2$—$Si(OEt)_3$, PhNH—$CH_2$—$Si(OMe)_3$, hexadecyl-$SiH_3$, $MeSi(OEt)_2H$, $PhSi(OEt)_2H$, $PhSi(OMe)_2H$, $MeSi(OEt)H_2$, propyl-$Si(OMe)_2H$, $MeSiH_3$, $MeSi(OEt)(OMe)H$, $(MeO)_3Si$—$CH_2CH_2$—$Si(OMe)_3$, $(EtO)_3Si$—$CH_2CH_2$—$Si(OEt)_3$, $Cl_3Si$—$CH_2CH_2$—$SiMeCl_2$, $Cl_3Si$—$CH_2CH_2$—$SiCl_3$, $Cl_3Si$—$(CH_2)_6$—$SiCl_3$, $(MeO)_3SiSi(OMe)_2Me$, $MeSi(OEt)_2Si(OEt)_3$, $MeSiCl_2SiCl_3$, $Cl_3SiSiCl_3$, $HSiCl_2SiCl_2H$, $HSiCl_2SiCl_3$, $MeSiCl_3$, $MeSiCl_2H$, $H_2C$=$CH$—$SiCl_3$, $PhSiCl_3$, $F_3C$—$CH_2$—$CH_2$—$SiCl_3$, $Cl$—$CH_2CH_2CH_2$—$SiCl_3$, $MeSi(OMe)Cl_2$, $MeSi(OEt)ClH$, $EtSiBr_3$, $MeSiF_3$, $Cl$—$CH_2$—$SiCl_3$, $Cl_2CH$—$SiCl_3$, $MeSiCl(OMe)_2$, $MeSiCl(OEt)_2$, $MeSi(OMe)Cl_2$.

Preference is given to $MeSi(OMe)_3$, $MeSi(OEt)_3$, $(H_3C)_2CHCH_2$—$Si(OMe)_3$ and $PhSi(OMe)_3$, with methyltrimethoxysilane or its hydrolysis/condensation product being preferred.

Examples of compounds of the general formula 1 in which a=2 are:
$Me_2Si(OMe)_2$, $Me_2Si(OEt)_2$, $Me_2Si(OCH(CH_3)_2)_2$, $MeSi(OMe)_2CH_2CH_2CH_3$, $Et_2Si(OMe)_2$, $Me_2Si(OCH_2CH_2OCH_3)_2$, $MeSi(OMe)_2Et$, $(H_3C)_2CH$—$Si(OMe)_2Me$, $Ph$-$Si(OMe)_2Me$, t-Bu-$Si(OMe)_2Me$, $Ph_2Si(OMe)_2$, $PhMeSi(OEt)_2$, $MeEtSi(OMe)_2$, $Me_2Si(OMe)Cl$, $Me_2Si(OEt)Cl$, $F_3C$—$CH_2$—$CH_2$—$Si(OMe)_2Me$, H$_2$C=CH—Si(OMe)$_2$Me, H$_2$C=CH—CH$_2$—Si(OMe)$_2$Me, Cl—CH$_2$CH$_2$CH$_2$—Si(OMe)$_2$Me, cy-Hex-Si(OMe)$_2$Me, n-Hex-Si(OMe)$_2$Me, cy-Hex-CH$_2$—CH$_2$—Si(OMe)$_2$Me, H$_2$C=CH—(CH$_2$)$_9$—Si(OMe)$_2$Me, Cl—CH$_2$—SiMe(OMe)$_2$, H$_2$N—(CH$_2$)$_3$—SiMe(OEt)$_2$, cyHex-NH—(CH$_2$)$_3$—SiMe(OMe)$_2$, H$_2$N—(CH$_2$)$_2$—NH—(CH$_2$)$_3$—SiMe(OMe)$_2$, O(CH$_2$CH$_2$)$_2$N—CH$_2$—SiMe(OMe)$_2$, PhNH—CH$_2$—SiMe(OMe)$_2$, (MeO)$_2$MeSi—CH$_2$CH$_2$—SiMe(OMe)$_2$, (EtO)$_2$MeSi—CH$_2$CH$_2$—SiMe(OEt)$_2$, (MeO)$_2$MeSiSi(OMe)$_2$Me, MeSi(OEt)$_2$SiMe(OEt)$_2$, Me$_2$Si(OMe)Si(OMe)$_3$, Me$_2$Si(OMe)Si(OMe)Me$_2$, Me$_2$Si(OMe)SiMe$_3$, Me$_2$Si(OMe)SiMe(OMe)$_2$.

Me$_2$SiCl$_2$, MeSiCl$_2$CH$_2$CH$_2$CH$_3$, Et$_2$SiCl$_2$, MeSiCl$_2$Et, (H$_3$C)$_2$CH—SiCl$_2$Me, Ph-SiCl$_2$Me, t-Bu-SiCl$_2$Me, Ph$_2$SiCl$_2$, PhMeSiCl$_2$, F$_3$C—CH$_2$—CH$_2$—SiCl$_2$Me, H$_2$C=CH—SiCl$_2$Me, H$_2$C=CH—CH$_2$—SiCl$_2$Me, Cl—CH$_2$CH$_2$CH$_2$—SiCl$_2$Me, cy-Hex-SiCl$_2$Me, cy-Hex-CH$_2$—CH$_2$—SiCl$_2$Me, H$_2$C=CH—(CH$_2$)$_9$—SiCl$_2$Me, Cl—CH$_2$—SiMeCl$_2$, Cl$_2$MeSi—CH$_2$CH$_2$—SiMeCl$_2$, Me$_2$SiClSiCl$_3$, Me$_2$SiClSiClMe$_2$, Me$_2$SiClSiMe$_3$, Me$_2$SiClSiMeCl$_2$. Preference is given to Me$_2$Si(OMe)$_2$, Me$_2$Si(OEt)$_2$, MeSi(OMe)$_2$CH$_2$CH$_2$CH$_3$ and Ph-Si(OMe)$_2$Me, with Me$_2$Si(OMe)$_2$ and MeSi(OMe)$_2$CH$_2$CH$_2$CH$_3$ being particularly preferred.

Me is the methyl radical, Et is the ethyl radical, Ph is the phenyl radical, t-Bu is the 2,2-dimethylpropyl radical, cy-Hex is the cyclohexyl radical, n-Hex is the n-hexyl radical, and hexadecyl is the n-hexadecyl radical.

Preference is given to a=1 or 2.

In particular, at least 50%, preferably at least 60%, and more preferably at least 70%, and not more than 80%, preferably not more than 90%, and more preferably not more than 100%, of all radicals R$^1$ in the compounds of the general formula 1 or the hydrolysis/condensation products thereof are methyl radicals, ethyl radicals or propyl radicals.

Although there is chemically no upper limit to the amount of water, the proportion of water should be kept as low as possible for economic reasons, since excess water has to be removed again. For this reason, a very small amount of water which is just sufficient to allow very largely complete hydrolysis and give clear to slightly turbid solutions is chosen. The solids content of the alkali metal organosiliconate solutions in a measurement using the solids content balance HR73 Halogen Moisture Analyzer from Mettler Toledo or a comparable measuring instrument at 160° C. is preferably at least 20% by weight, more preferably at least 40% by weight, preferably not more than 70% by weight and more preferably not more than 60% by weight.

In the case of alkoxysilanes or hydrolysis/condensation products thereof as starting materials, the alcohol liberated is distilled off to such an extent that a residual concentration in the aqueous alkali metal organosiliconate solutions of less than 0.1% by weight, more preferably not more than 0.02% by weight, and in particular not more than 0.01% by weight, of alcohol, in particular of the formula HOR$^4$, results.

In the case of nalosilanes or mixed haloalkoxysilanes, in particular of the general formula 1 in which Y is F, Cl or Br, or hydrolysis/condensation products thereof as starting material, these are preferably firstly reacted with water to form the organosilicic acid and also hydrogen halide, possibly together with alcohol, in particular HY. Aqueous solutions of the alkali metal organosiliconates are prepared from this organosilicic acid using alkali metal hydroxide. In the first step, the amount of water is chosen so that, and the organosilicic acid is optionally washed with water so that, a residual concentration of halide anions, in particular Y, in the aqueous alkali metal organosiliconate solutions of not more than 0.3% by weight, more preferably not more than 0.1% by weight, and in particular not more than 0.01% by weight, results.

A direct reaction of nalosilanes of the general formula (1) having Y=Cl, F, Br or hydrolysis/condensation products thereof with a basic alkali metal salt is likewise within the scope of the invention but not preferred for economic reasons since the hydrogen halide formed consumes an equimolar amount of basic alkali metal salt, which additionally has to be taken into account when determining the amount required for alkali metal siliconate formation. Apart from this additional consumption of basic alkali metal salt, the economics are made poorer by two further effects: the proportion of alkali metal halide salt which has been formed and cannot be separated off has no hydrophobicizing effect and thus reduces the efficiency of the alkali metal siliconate as hydrophobicizing agent, and the hydrogen halide, preferably HY, is not recovered and is thus lost to the production process.

Owing to the almost complete recycling of the dissociation products, in particular HCl and methanol, the continuous process described in DE 4336600, in which an organoalkoxysilane, in particular of the general formula 1 where Y=OR$^4$, is reacted directly with aqueous alkali metal hydroxide with liberation of alcohol, in particular HOR$^4$, to give aqueous alkali metal organosiliconate solution, is particularly suitable for the preparation of aqueous solutions of alkali metal organosiliconates.

The basic alkali metal salts preferably have a pK$_b$ of not more than 12, more preferably not more than 10, and in particular not more than 5. As basic alkali metal salts, use is made of compounds which form solvated hydroxide ions in water and contain alkali metal ions as cations. Preference is given to using alkali metal hydroxides such as lithium hydroxide, sodium hydroxide, potassium hydroxide and cesium hydroxide, more preferably sodium, hydroxide and potassium hydroxide, as alkali metal salts. Further examples of alkali metal salts are alkali metal carbonates such as sodium carbonate and potassium carbonate and also alkali metal hydrogencarbonates such as sodium hydrogencarbonate, alkali metal formates such as potassium formate, alkali metal silicates (water glass) such as sodium orthosilicate, disodium metasilicate, disodium disilicate, disodium trisilicate or potassium silicate. Furthermore, it is also possible to use alkali metals directly, alkali metal oxides, alkali metal amides or alkali metal alkoxides, preferably those which liberate the same alcohol as the compounds of the general formula 1 which are used.

It is also possible to use mixtures of various salts, optionally of different alkali metals, for example mixtures of sodium hydroxide and potassium hydroxide. Typical secondary constituents in industrial grades of the basic salts (i.e. at purities in the range from 80 to 99% by weight), e.g. water or other salt components, e.g. proportions of sodium, in potassium salts or carbonates in hydroxides, generally do not interfere and can be tolerated. A further preferred variant, is the use of alkali metal organosiliconates, in particular aqueous or aqueous-alcoholic preparations of alkali metal organosiliconates, optionally in admixture with other alkali metal salts, preferably alkali metal hydroxides. This may be advantageous when the siliconate or the aqueous or else aqueous-alcoholic siliconate preparation (solution, suspension, emulsion) is, for example, in any case produced in large quantities as a sales product, so that only a further reaction step is required in order to produce the powders (P).

For example, a compound of the general formula 1 can be reacted with an aqueous solution of a potassium methylsiliconate (e.g. WACKER SILRES® BS 16). Preferred compounds of the general formula 1 which are reacted with commercially available alkali metal methylsiliconates include Me-Si(OMe)$_3$, Et-Si(OMe)$_3$, Ph-Si(OMe)$_3$, propyl-Si(OMe)$_3$, butyl-Si(OMe)$_3$, hexyl-Si(OMe)$_3$, octyl-Si(OMe)$_3$, vinyl-Si(OMe)$_3$ and their possible constitutional isomers or stereoisomers, where Me is the methyl radical, Et is the ethyl radical, Ph is the phenyl radical, propyl is a 1-propyl or 2-propyl radical, butyl is an n-butyl radical or a branched butyl radical, octyl is an n-octyl radical or a branched octyl radical or an octyl radical having cyclic structures, hexyl is an n-hexyl radical or a branched hexyl radical or a hexyl radical having cyclic structures, each of which are bound to si at any carbon atom, and vinyl is a vinyl radical. This route is particularly advantageous when siliconate powders are to be produced which contain not only methyl radicals but also other radicals $R^1$ and $R^2$.

The removal of water from the aqueous alkali metal organosiliconate solution, also referred to as drying, is preferably effected by drying in a spray dryer. Drying is carried out in air or under inert gas (e.g. nitrogen, argon, helium, lean air containing a maximum of 2% of oxygen). Spray drying is preferably carried out at the pressure of the surrounding atmosphere, but it can also be carried out under a pressure which has been reduced or increased compared to atmospheric pressure. The pressure is preferably at least 10 hPa, more preferably at least 100 hPa, and not more than 2000 hPa, more preferably not more than 1200 hPa absolute.

Spray drying can be carried out in any apparatuses which are suitable for the spray drying of liquids, and are already widely known, for example those having a two-fluid nozzle, a cemented carbide nozzle or hollow cone nozzle or a swirling atomizer nozzle or having a rotating atomizer disk, in a heated dry gas stream. The entry temperature of the dry gas stream, where the spraying gas is preferably air, lean air or nitrogen, into the spray drying apparatus is preferably from 110° C. to 350° C., more preferably at least 110° C. and not more than 250° C., and in particular at least 110° C. and not more than 180° C. The exit temperature of the gas stream formed during drying is preferably from 40 to 120° C., in particular from 60 to 110° C. The spraying gas can, if necessary, in order to produce a lower residual moisture content, be heated to temperatures of up to 250° C., preferably in the range from 40 to 200° C., and more preferably from 50 to 150° C. The spraying pressure is preferably at least 500 hPa, more preferably at least 800 hPa, and not more than 500,000 hPa, in particular not more than 10,000 hPa. The speed of rotation of the atomizer disk is mainly in the range from 4000 to 50,000 rpm, with the individual decomposition temperatures having to be drawn upon for optimal setting of the spraying parameters. A great advantage of the spray drying process is that, owing to the small volume in the hot nozzle region, states which are critical to safety are not to be expected, even in the temperature range of the thermal decomposition. Excessively high temperatures/residence times are reflected, owing to elimination of the radicals $R^1$, $R^2$, in a reduced hydrophobicizing action of the dried alkali metal organosiliconate, which can be checked and corrected simply by a person skilled in the art.

The spray drying is preferably implemented in a spray dryer. Spray drying in this case can be carried out in such a way that particle formation occurs directly from the aqueous alkali metal organosiliconate solution or by a fluidized bed of previously dried alkali metal organosiliconate solution being placed in the spray dryer and the alkali metal organosiliconate solution being sprayed onto this. In parallel to the alkali metal organosiliconate solution, further liquids such as solvents, preferably water or alcohols or surfactants, can be fed into the dryer, e.g. in order to alter the spraying pattern by means of surface effects.

Further constituents can be added to the aqueous solutions of alkali metal organosiliconates before spray drying, e.g. in order to improve the use properties of the solid (S). To improve and maintain free-flowing behavior, flow aids and/or anticaking agents can be added. Constituents of the building material mixture to be produced using the solid (S), for example gypsum plaster, cement, sand, glass or fillers such as chalks, silicates, clays, silicas, metal oxides, polymers (for example PVA, PVC, PE, PP, polystyrene, PTFE, PVDF in powder form or as pellets) and also setting retarders or accelerators or else liquid polymers such as mineral oils or silicone oils, can also be added at the beginning, during or at the end of the production process.

Preference is given to adding not more 50, more preferably not more than 10 parts by weight of further constituents per 100 parts by weight of alkali metal organosiliconates.

The dried solid (S) is discharged via customary discharge devices such as discontinuous locks, star feeders or cyclones into the attached process apparatuses (for example mills, sifters, sieves) or storage or transport containers (for example silos, containers, Big Bags, sacks, drums, hobbocks). These can be cooled or heated in order to bring the solid (S) to the temperature which is desired in each case.

The solid (S) preferably has a solids content determined at 160° C. by means of the solids content balance HR$^{73}$ Halogen Moisture Analyzer from Mettier Toledo or a comparable measuring instrument of at least 96% by weight, more preferably at least 98% by weight, and in particular at least 99% by weight. It contains not more than 2% by weight, preferably not more than 0.5% by weight, and in particular not more than 0.1% by weight, of halide ions determinable by means of elemental analysis. It preferably has an alcohol content of not more than 0.2% by weight, more preferably not more than 0.1% by weight, yet more preferably not more than 0.05% by weight, still more preferably not more than 0.01% by weight and in particular not more than 0.005% by weight. The alcohol content encompasses both the chemically bound alcohol and adsorbed alcohol. It is preferably determined on a solution of the powder by means of NMR spectroscopy. The addition of base, preferably alkali metal hydroxide, can be useful here in order to ensure solubility. As reference parameters, it is possible to employ the proportions by weight of all siloxy units $(R^1)_a Si(O_{1/2})_b [(-Si(R_2)_{3-c}(O_{1/2})_c]_d$ derived from the formula 1, for example $(R^1)_a Si(O_{1/2})_b [(-Si(R_2)_{3-c}(O_{1/2})_c]_d$ or $(R^1)_a Si(O_{1/2})_b$, and the proportions by weight of the alkoxy units $R^4 O_{1/2}$ and the proportions by weight of the free alcohol $P^4 OH$. Determination of the alcohol content is preferably carried out on the basis of the molar percentages of the specified fragments as can be determined from the $^1$H-NMR Spectrum and the molar masses thereof, with the masses/proportions by weight of the fragments $R^4 O_{1/2}$ present and of the free alcohol $R^4 OH$ being added up and the sum thereof being reported as alcohol content.

The particle size distribution can be influenced within certain limits by the spray drying parameters. In general, the solids (S) produced according to the invention display excellent powder flow.

The bulk density is preferably below 700 g/l, more preferably below 600 g/l, and in particular below 500 g/l.

The invention also provides solids (S) which can be produced by the above process, the building material mixtures provided therewith, which include, for example, gypsum- or cement-based dry mortars, plasters and renders, knifing fillers, fine knifing fillers, self-levelling compositions, on-site concrete and spray concrete, and also components and moldings produced therefrom.

All above symbols in the above formulae have their meanings independently of one another. In all formulae, the silicon atom is tetravalent.

Unless indicated otherwise in each case, all amounts and percentages indicated in the following examples and comparative examples are by weight and all reactions are carried out at a pressure of 1000 hPa (abs.).

The solids content is in each case determined using the solids content balance HR73 Halogen Moisture Analyzer from Mettler Toledo at 160° C. The methoxy/methanol content was determined as described above by means of $^1$H-NMR spectroscopy.

Production Example 1 (According to the Invention): Drying of an Aqueous Solution of Potassium Methylsiliconate (WACKER SILRES® BS16 Wacker Chemie AG) by Spray Drying In a fluidized-bed spray dryer GPCG 3.1 from Glatt, a commercially available solution of potassium methylsiliconate (WACKER SILRES® BS 16) is sprayed from above at an inflow air temperature of 140-145° C. into the spray chamber at a pressure of 2000 hPa by means of a straight 1.6 ram two-fluid nozzle. The spraying air temperature is 100-105° C., and the exhaust air temperature is 95-80° C. A white free-flowing powder having a solids content of 96.71% by weight and a bulk density of 480 g/l is isolated. Owing to its maximum particle size of 200 µm, it is suitable without further milling or classification steps for use as a dry mix hydrophobicizing additive. In addition, it displays surprisingly low hygroscopic behavior so that it retains its excellent powder flow capability even after a few hours in air. According to particle size analysis (Sympatec Helos particle size analysis, dispersion pressure in the dry disperser: 4 bar), 100% of all particles are smaller than 174 µm, 99% of all particles are smaller than 130.70 µm, 90% of all particles are smaller than 38.00 µm, 50% of all particles are smaller than 9.04 µm and 10% of all particles are smaller than 1.78 µm. The maximum of the distribution density is at 10 µm. 10.18% of all particles are below 1.80 µm. Elemental analysis indicates a potassium content of 30 g/100 g of powder and a silicon content of 21 g/100 g of powder, which suggests the following average formula for the potassium methylsiliconate: $H_3C-Si(OH)_{1.9744}(OK)_{1.0256}$.

Comparative Example 1 (Not According to the Invention): Drying of an Aqueous Solution of Potassium Methylsiliconate (WACKER SILRES® BS 16 Wacker Chemie AG) by Drying in a Powder Bed (as Described in WO 2013/075969)

In a horizontal paddle dryer (stainless steel cylinder, length 2200 mm, diameter 380 mm, with wiper and transport elements arranged in a circle on the central rotor) heated by means of heat transfer oil, a commercially available solution of potassium methylsilieonate (WACKER SILRES® BS 16, Wacker Chemie AG) is metered continuously onto a powder bed of dried potassium methylsiliconate at a speed of rotation of 300 min$^{-1}$, a wall temperature of 190° C. and 87 hPa. The volatile constituents are conveyed via two domes to an essentially horizontal shell-and-tube heat exchanger operated using cooling-water and condensed out there. At the end of the paddle dryer, the dried powder is discharged via a discontinuous solids lock. Speed of rotation and introduction rate give an average residence time in the drying plant of about 6 minutes. A white free-flowing powder having a solids content of 98.49% by weight and a bulk density of 870 g/l is isolated. Owing to the presence of coarse particles having diameters of up to 1 mm, the powder has to be milled for use as dry mix hydrophobicizing additive. Only after milling and sifting are the particle sizes in the range conforming to the application. According to particle size analysis (Sympatec Belos particle size analysis, dispersion pressure in the dry disperser: 4 bar), 100% of all particles are smaller than 174 µm, 99% of all particles are smaller than 137.51 µm, 90% of all particles are smaller than 50.90 µm, 50% of all particles are smaller than 6.20 µm and 10% of all particles are smaller than 1.07 µm. 22.86% of all particles are below 1.80 µm. It follows therefrom that, compared to production example 1 according to the invention, a significantly higher proportion of fine dust is formed in comparative example 1 (not according to the invention) as a result of the milling and sifting, and this represents a further disadvantage; in terms of safety reasons in use. The maximum of the distribution density is at 12 µm.

Use Examples 1 and 2: Hydrophobicization of a Commercial Structural Gypsum Plaster Using the Potassium Methylsiliconate Powder from Production Example 1 and Comparative Example 1 (Molar Ratio of Alkali Metal to Silicon: 1.04)

In the case of use examples 1 and 2, table 1 shows that the potassium methylsiliconate powder from production example 1 reduces the 2 h water absorption at an addition of 0.20% by weight to a significantly greater extent than the potassium methylsiliconate powder from comparative example 1 (not according to the invention).

In the use examples, the commercial structural gypsum plaster was used in powder form. 0.20% by weight of potassium methylsiliconate powder from production example 1 (according to the invention) and from comparative example 1 (not according to the invention) was in each case added in dry form to the dry mortar and the mixtures were effectively mixed for 30 seconds in a planetary mixer as described in EN 196-1.

This dry mixture was subsequently added a little at a time while stirring to the make-up water in accordance with the formulation indicated on the pack and stirred by means of the planetary mixer as described in EN 196-1 to give a homogeneous slurry (according to the pack: 300 g of powder and 200 g of water). The slurry obtained was subsequently poured into PVC rings (diameter: 80 mm, height 20 mm) and setting of the gypsum plaster at 23° C. and 50% relative humidity over 24 hours was awaited. After removal of the gypsum, test specimens from the rings, the test specimens were dried to constant weight at 40° C. in a convection drying oven. To determine the water absorption by a method based on DIN EN 520, the test specimens were, after determining the dry weight, stored underwater for 120 minutes, with the specimens being laid horizontally on metal meshes and the height of water over the highest point of the test specimens being 5 mm. After 120 minutes, the test specimens were taken from the water, allowed to drip on a sponge saturated with water and the percentage water absorption after 120 minutes was calculated on a balance having a precision of 0.01 g from the wet weight and the dry weight according to the formula Percentage water absorption={[mass(wet)−mass(dry)]/mass(dry)}·100%.

TABLE 1

Comparison of the properties of WACKER SILRES ® BS16 spray dried according to the invention and dried in a powder bed

| | According to WO 2013/075969 (not according to the invention: dried in a powder bed) | According to the invention (spray dried) |
|---|---|---|
| Particle size distribution, upper limit X100 | 1000 μm | 200 μm |
| Hygroscopic increase in weight after 20 hours at 23° C./50% relative atmospheric humidity | 37.9% | 32.3% |
| State of matter after 48 hours at 23° C./50% relative atmospheric humidity | Liquid | Solid, particulate, free-flowing |
| Powder spread (powder flow) *) | 90 mm | 101 mm |
| Water absorption of gypsum plaster** | 16.9% | 1.59% |

*) Diameter of the spread-out cone after lifting a cylinder which had an internal diameter of 35 mm and a height of 51 mm and had been loosely filled with powder up to the upper edge (not compacted)
**) Addition of 0.20% by weight of powder to a commercial structural gypsum plaster; water absorption without hydrophobicizing additive: 37.4%

The invention claimed is:

1. A process for producing a pulverulent solid comprising one or more alkali metal organosiliconates, comprising: spray drying an aqueous solution of one or more alkali metal organosiliconates prepared by reacting one or more organosilanes of the formula 1

$$(R^1)_a Si(Y)_b (\!-\!Si(R^2)_{3-c}(Y)_c)_d \qquad (1)$$

or hydrolysis/condensation products thereof, or by reaction of organosilanes of the formula 1 and also hydrolysis/condensation products thereof, with water and a basic alkali metal salt, and removing liberated dissociation products HY, where
$R^1$, $R^2$ are each a methyl radical,
Y is hydrogen, F, Cl, Br or $OR^4$ and
$R^4$ is a methyl, ethyl, 1-propyl or 2-propyl group,
a is 1, 2 or 3 and
b, c, d are each 0, 1, 2 or 3,
with the proviso that $b+c \geq 1$ and $a+b+d=4$,
where the amount of basic alkali metal salt is such that there is at least 0.1 mol and not more than 3 mol of alkali metal cations per 1 mol of silicon,
wherein the alkali metal organosiliconate(s) have a molar ratio of alkali metal to silicon of from 0.1 to 3, and prior to spray drying, have a content of alcohol of less than 0.02% by weight, and a content of halide anions of not more than 1% by weight.

2. The process of claim 1, wherein the basic alkali metal salt is selected from the group consisting of alkali metal hydroxides, alkali metal silicates, alkali metal organosiliconates and mixtures thereof.

3. The process of claim 1, wherein water is removed in an amount so as to provide a solids content, determined at 160° C., of at least 96% by weight based on the total weight of the pulverulent solid.

4. The process of claim 1, wherein the alcohol content of the pulverulent solid is not more than 0.05% by weight based on the total weight of the pulverulent solid.

* * * * *